US007639862B2

(12) United States Patent
Canning, Jr. et al.

(10) Patent No.: US 7,639,862 B2
(45) Date of Patent: Dec. 29, 2009

(54) METHOD AND APPARATUS FOR QUANTIFYING PIGMENT DISPERSION QUALITY BY PAINT DRAWDOWN

(75) Inventors: Robert Vincent Canning, Jr., Bear, DE (US); Scott Richard Mehr, Dickson, TN (US); Barry Rubin, Glen Mills, PA (US); Thomas William Simpson, III, Boothwyn, PA (US); Douglas Ray Stilwell, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 774 days.

(21) Appl. No.: 11/298,958

(22) Filed: Dec. 9, 2005

(65) Prior Publication Data

US 2007/0146702 A1 Jun. 28, 2007

(51) Int. Cl.
*G06K 9/00* (2006.01)
*G01N 21/55* (2006.01)

(52) U.S. Cl. ....................................... 382/141; 356/445

(58) Field of Classification Search ......... 382/141–152; 356/445; 501/11–32

See application file for complete search history.

(56) References Cited

U.S. PATENT DOCUMENTS 2,626,707 A * 1/1953 Whately ........................ 209/5
3,573,081 A * 3/1971 Dietz ......................... 106/448
4,445,365 A * 5/1984 Selby ........................ 73/54.34
4,450,095 A * 5/1984 Finlayson ................... 516/101
4,832,984 A * 5/1989 Hasegawa et al. ........... 427/161
5,249,029 A 9/1993 Sommer et al.
5,268,749 A 12/1993 Weber et al.
5,341,824 A * 8/1994 Fletcher et al. ............. 131/281
5,474,844 A * 12/1995 Sato et al. ................... 428/332
5,773,492 A * 6/1998 Ferguson .................... 523/171
5,811,481 A * 9/1998 Boutier et al. .............. 524/313
6,055,329 A * 4/2000 Mufti ......................... 382/152
6,177,486 B1 * 1/2001 Ferguson .................... 523/161
6,306,931 B1 * 10/2001 Ferguson .................... 523/161
6,409,567 B1 * 6/2002 Amey et al. ................... 445/50

(Continued)

OTHER PUBLICATIONS

CL2426 PCT International Search Report.

(Continued)

*Primary Examiner*—Manav Seth

(57) ABSTRACT

An automated computer-controlled method and apparatus for measuring the quality or fineness of a pigment dispersion sample, comprising placing the pigment dispersion at the deep end of the tapered path of a Hegman gage block, placing the Hegman gage block in a holder in a motorized drawdown device that draws the scraper along the length of the tapered path at an angle and to at a contact pressure and at a controlled rate, thereby creating a tapered film sample of paint whose thickness tapers from a maximum thickness of 100 micrometers to a minimum thickness of zero. An illuminator assembly illuminates the sample with a substantially collimated light source at an intensity level and the light reflected from the sample is collected by a lens onto a photodetector array in a digital camera. After a time interval the camera acquires an image of the sample. The image is digitized and stored in a memory in the computer and then a portion of the image within a region of interest corresponding to the sample in the tapered path is analyzed to detect and count pigment agglomerates that protrude above the surface of the sample.

10 Claims, 11 Drawing Sheets

U.S. PATENT DOCUMENTS

| | | | | |
|---|---|---|---|---|
| 6,696,375 | B2 * | 2/2004 | Welsh et al. | 501/12 |
| 6,721,055 | B2 | 4/2004 | Hatfield et al. | |
| 7,176,329 | B2 * | 2/2007 | Smith et al. | 560/263 |
| 2002/0067485 | A1 | 6/2002 | Hatfield et al. | |
| 2002/0174804 | A1 | 11/2002 | Rodrigues et al. | |
| 2004/0095573 | A1 | 5/2004 | Tsai et al. | |

OTHER PUBLICATIONS

ASTM Standard D 1210-96—"Standard Test Method for Fineness of Dispersion of Pigment-Vehicle Systems by Hegman-Type Gage".

* cited by examiner 14
12
M1
32
34F
34
40
42F
42
10
M2
s
20
22D
36
60
30
22B

DATA BUS
14
D
K
DISPLAY
KEYBOARD
14M
14FD
14CD
14Z
G
CPU
100
A/D
120
16
MEMORY 14R
10
12
40
42
44
50
60
62
64
66
70
75
80

METHOD AND APPARATUS FOR QUANTIFYING PIGMENT DISPERSION QUALITY BY PAINT DRAWDOWN

BACKGROUND OF THE INVENTION

Pigment dispersion quality in paint has traditionally been evaluated by trained human operators who make visual observations of the surface appearance of a paint "drawdown" sample. The drawdown evaluation typically uses a device known as a "Hegman Fineness Gage", usually referred to as a "Hegman Gage", as described in American Society for Testing and Materials (ASTM) Standard D1210 "Standard Test Method for Fineness of Dispersion of Pigment-Vehicle Systems by Hegman-Type Gage". The Hegman Gage comprises a hardened steel (or stainless steel or chrome-plated steel) block (called a Hegman Gage Block) and a hardened scraper of similar material. The hardened steel block has a flat ground planar surface and has a tapered path machined along its 127 millimeter length. The tapered path is 100 micrometers deep at one end and the path tapers to a depth of zero at its other end. The Hegman Gage for manual drawdowns has a one-half inch wide path. Calibration scales are marked along the lateral edges of the path. Along one edge the scale is marked in micrometers (designating the depth of the tapered path) and along the other edge the scale is marked in "Hegman Units", ranging from zero to eight, which correspond to a depth of 100 micrometers for a Hegman Unit of zero ranging to a depth of zero for a Hegman Unit of 8.

A paint or paste sample is mixed with a vehicle (usually an alkyd resin) and is prepared using well known methods. A predetermined quantity of paint or paste is deposited at the deep end of the tapered path of the Hegman gage block. The hardened steel scraper is placed on the steel block and drawn along its length, leaving behind, in the tapered path, a film-like deposit of paint whose thickness tapers from a maximum thickness to a minimum thickness.

The operator visually observes the sample and looks for pigment agglomerates that protrude from the paint film surface. These protrusions are known as "particles", "specks" or "scats". The operator visually determines the location along the gage where the specks first appear. Because the appearance of the drawdown sample changes as the paste or paint sample begins to dry, a visual observation must be made immediately. Within about ten seconds of the drawdown the operator makes a visual observation of the appearance of the drawdown sample. The operator determines the point along the gage where a definite pattern of specks appear. This point is called the "fineness line" or "fineness measurement" and provides an indication of the fineness or quality of the dispersion of the pigment. The operator also determines the locations of specks and counts them in predetermined ranges along the gage block. Although conducted under controlled lighting conditions these observations are still somewhat subjective.

Because this ASTM D1210 measurement protocol relies upon the expertise of human operators, both for the manual drawing of the hardened steel scraper along the length of the Hegman gage block and for making a visual observation, test results vary from operator to operator and thus lack repeatability. The ASTM measurement results are believed to be more qualitative than quantitative in nature.

Previous devices attempt to provide a quantitative evaluation of pigment dispersion quality in paint. Examples of such devices, which are described in U.S. Pat. Nos. 6,721,055 and 5,249,029, still suffer from certain deficiencies. Both of these devices operate in a so called "dark field" optical mode, i.e., they only collect light scattered from surface anomalies and ignore light reflected from the surface. In a dark field operation, light reflected from the surface of a paint film sample is blocked from reaching a photodetector and only light scattered from pigment agglomerates that protrude above the film surface reach the photodetector. Both of these devices illuminate only a small portion of the paint film sample at a time and require movement of the Hegman gage block (also referred to as a "grindometer block") past an illuminator and photodetector arrangement, an inherently slow operation that typically takes several seconds. A wet paint film sample begins to dry immediately and changes in appearance as it dries. In the previous devices different portions of a freshly prepared wet film sample are imaged at different times, thus providing different levels of sensitivity on different portions of the paint film samples.

Because of the lack of repeatability of the visual method and the deficiencies of the previous dark field imaging methods, it is believed that there is a need for an improved imaging method and for a more quantitative evaluation of the drawdown sample appearance to provide accurate characterization of pigment dispersion.

SUMMARY OF THE INVENTION

The present disclosure relates to an automated computer-controlled method and apparatus for measuring the quality or fineness of a pigment dispersion.

In a first aspect the disclosure is directed to a method for measuring the quality of a pigment dispersion in a paint or paste sample comprising:

a) depositing a quantity of the paint or paste at a deep end of a tapered path of a Hegman gage block in sufficient quantity to substantially fill the tapered path;
b) placing a scraper on the Hegman gage block and, using a motorized drive, drawing the scraper along the length of the tapered path at an angle to the plane of the block and at a contact pressure sufficient to create a film-like sample having a tapered thickness;
c) exposing the film-like sample to a substantially collimated light source at a light intensity level sufficient to illuminate the film-like sample;
d) acquiring a bright field image of light reflected from the film-like sample with a camera having a two-dimensional photodetector array, digitizing and storing the image in a computer memory; and
e) analyzing the image within a region of interest corresponding to the tapered path to detect agglomerates in the pigment that protrude above the surface of the film-like sample. The paint or paste sample can be prepared by combining the pigment to be measured with a resin.

In a second aspect, the disclosure relates to an automated computer-controlled method for measuring the quality of a pigment dispersion, the pigment dispersion being prepared by: i) combining a suitable resin with the pigment to be measured to form a paint or paste; and ii) depositing a quantity of the paint or paste at a deep end of a tapered path of a Hegman gage block in sufficient quantity to substantially fill the tapered path, the method comprising:

a) placing the Hegman gage block in a holder in a motorized drawdown device, the holder sensing the presence of the gage block and signaling the computer that the gage block is present;
b) activating the motorized drawdown device to lower a scraper onto the Hegman gage block and drawing the scraper along the length of the tapered path at an angle to the plane of the block and at a contact pressure sufficient to form a tapered film sample whose thickness tapers from a maximum thickness of over one hundred microns to a minimum thickness of zero;

c) waiting a time interval;

d) arranging a light source, a first spherical mirror, the sample, a second spherical mirror, a lens, and a camera having a two-dimensional photodetector array, in a bright field arrangement, so that the light source and the first spherical mirror are capable of illuminating the sample in a substantially collimated manner at a light intensity level sufficient to reflect light rays from the sample to the second spherical mirror whereby the second spherical mirror is capable of directing the light rays to the lens of the camera;

e) acquiring an image of the sample with the two-dimensional photodetector array;

f) digitizing and storing the image in a memory in the computer; and g) analyzing the image within a region of interest corresponding to the tapered film sample along the tapered path to detect and count agglomerates in the pigment that protrude above the surface of the sample. Step d) can further comprise:

1) creating a calibration image of a calibration standard by illuminating the calibration standard with the substantially collimated light source, 2) capturing an image of the calibration standard, 3) calculating the average grey level of the image, and 4) adjusting the intensity of the light source so that the average gray level is within a range, thereby establishing a light intensity level sufficient to illuminate the sample.

In this second aspect, the method can further comprise: creating a frame-averaged dark current image representing the response of the photodetector array in the absence of light; and storing the frame-averaged dark current image in the computer memory.

In this second aspect, the step (e) of acquiring the image of the sample can further comprise:

1) collecting the light reflected from the surface of the sample with the second spherical mirror and directing the collected light to a lens;

2) using the lens to project an image of the sample surface onto a two-dimensional photodetector array to create an electrical signal representative of the image;

4) digitizing the electrical signal using an analog to digital converter;

5) frame averaging the electrical signal;

6) storing the frame-averaged digitized representation of the image as an array of picture elements in a computer memory;

7) creating a dark-current-corrected frame-averaged image by subtracting the frame-averaged dark-current image from the frame-averaged image of the sample on a pixel by pixel basis.

In this second aspect step g) of analyzing the image can further comprise:

1) for each pixel within the region of interest, that pixel having a pixel intensity, determining an average grey level of a first number of pixels surrounding that pixel, 2) calculating a ratio of the pixel intensity to the average grey level; and 3) comparing the ratio to a threshold to detect one or more contiguous pixels that represent agglomerates in the pigment that protrude above the surface of the sample.

In this second aspect the first number of pixels surrounding that pixel excludes a second, smaller, number of pixels immediately adjacent to that pixel.

Also, this second aspect can further comprise;

h) tracing the contiguous detected pixels of step g) to identify discrete agglomerates;

i) determining the position of each identified discrete agglomerate along a plurality of parallel channels along the tapered path of the Hegman gage block;

j) reporting the position of each identified discrete agglomerate in a visual display.

In this second aspect the calibration standard can be comprised of a reflectance standard.

In the second aspect the calibration standard can be comprised of a glass sheet in the shape of the Hegman gage block, the glass sheet having a back surface painted white to optically simulate the surface of a pigment dispersion sample and a front surface having a plurality of epoxy droplets thereon, the droplets optically simulating pigment agglomerates protruding from the pigment dispersion sample.

In a third aspect, the disclosure relates to an apparatus for measuring the quality of a pigment dispersion, the apparatus comprising:

a) a light-tight enclosure comprising a sample holder, an illuminating assembly for illuminating the sample with substantially collimated light at an intensity level, and an imaging assembly, b) a computerized image processing assembly for controlling the illumination level of the sample by the illuminating assembly and for receiving images created by the imaging assembly and analyzing those images, wherein:

(1) the sample holder comprises a support frame, a Hegman gage block drawdown assembly for holding the sample to be measured in a plane and a motorized drawdown mechanism, (2) the illuminating assembly comprises:

i) a source of light, a reflector, and a fiber optic light bundle, the reflector reflecting light from the light source to an end of the fiber optic bundle proximal to the light source and the distal end being positioned to project light in a first direction;

ii) a first spherical mirror having a first focal length, the mirror being positioned about one focal length from the distal end of the fiber optic bundle and oriented to receive the light from the fiber optic bundle and to reflect the light to illuminate the sample with a beam of substantially collimated light; and (3) the imaging assembly comprises:

(i) a second spherical mirror, ii) a lens having a stop, iii) a two-dimensional photodetector array, and iv) a computerized image processing assembly, the second spherical mirror having a second focal length, the second spherical mirror being positioned one focal length from the lens and oriented to receive light directly reflected from the sample and to focus the light from the sample onto the stop of the lens;

the lens focusing an image of the sample onto the two-dimensional photodetector array, each photodetector in the array creating an electrical signal representative of the light reflected from a respective location on the surface of the sample, the photodetector array being electrically connected to the computerized image processing assembly, the electrical signal from each photodetector being transmitted to the computerized image processing assembly, the amplitude of the signal being digitized and stored in a memory as a two dimensional array of pixels, and the computerized image processing assembly being under control of a software program to process the two dimensional array of pixels to detect and analyze pigment agglomerates that protrude above the surface of the sample.

The method of the present invention can comprise placing the Hegman gage block in a holder in a motorized drawdown device. A switch in the holder senses the presence of the gage block and signals the computer that the gage block is present. The motorized drawdown device is activated, by an operator, to lower a hardened steel scraper onto the Hegman gage block, typically at a predetermined angle, and to draw the scraper along the length of the tapered path at a contact pressure, which can be predetermined, and at a rate, thereby creating a tapered film sample of paint whose thickness tapers from a maximum thickness of 100 micrometers to a minimum thickness of zero. The drawdown device signals the computer when the drawdown is complete. An illuminator assembly illuminates the sample with a substantially collimated light source at an intensity level which can be predetermined. A fiber optic assembly receives light from a light source and directs the light to a spherical mirror which collimates the light and directs it to illuminate the sample. The light reflected from the sample is collected by a second spherical mirror which directs the light to a lens that images the light onto a photodetector array in a digital camera. After waiting a time interval that can be predetermined the computer signals the camera to acquire an image of the sample. The image is digitized and stored in a memory in the computer. The computer then analyzes the image within a region of interest corresponding to the sample along the tapered path to detect and count pigment agglomerates that protrude above the surface of the sample.

The apparatus and method of the present invention provide several advantages over the ASTM D1210 visual method and over the previous optical detection methods. A motorized drawdown is performed that is more repeatable than a manual drawdown. A substantially collimated light beam at a calibrated light level is used to illuminate the drawdown sample. A bright field image of the entire surface of the drawdown sample is captured by a charge coupled device (CCD) camera at a precise time instant at a predetermined time interval after the drawdown. The image of the sample is digitized for analysis by a computer image processing program. Counting of specks is based on objective criteria and is more reproducible than judgments by a human operator. A larger area is analyzed for each drawdown since a modified Hegman gage having a 4-inch wide tapered path is used instead of a gage having a ½-inch wide tapered path, thus providing improved statistical results over those obtainable by the ASTM method or the previous optical detection methods.

The method and apparatus provides a video image analysis for assessing pigment dispersion quality using a mechanized paint drawdown on a Hegman Gage. The number of pigments agglomerates that protrude from the paint surface (scats) between the Fineness Line and the Stop Point are automatically determined.

Drawdowns performed on the four-inch wide Hegman Gage can result in an image of the sample which is analyzed in a specified number of channels (for example, eight) across the four inch width of the tapered path. The detection of scats is based on their optical contrast with the white paint background. By establishing a "shape factor" for detected artifacts, (i.e., agglomerates or particles) in the image, streaks caused by large agglomerates may be identified and not counted if desired.

In order to periodically confirm instrument operation and to recalibrate the light level, a Gage with a simulated sample can be used as a calibration standard (See FIG. 11). This calibration standard simulates a pigment dispersion sample, whose characteristics are known and which should produce known numerical results, for periodically checking the operation of the unit.

In one embodiment, the invention herein can be construed as excluding any element or process step that does not materially affect the basic and novel characteristics of the composition or process. Additionally, the invention can be construed as excluding any element or process step not specified herein.

DETAILED DESCRIPTION OF THE INVENTION

Figure 1:
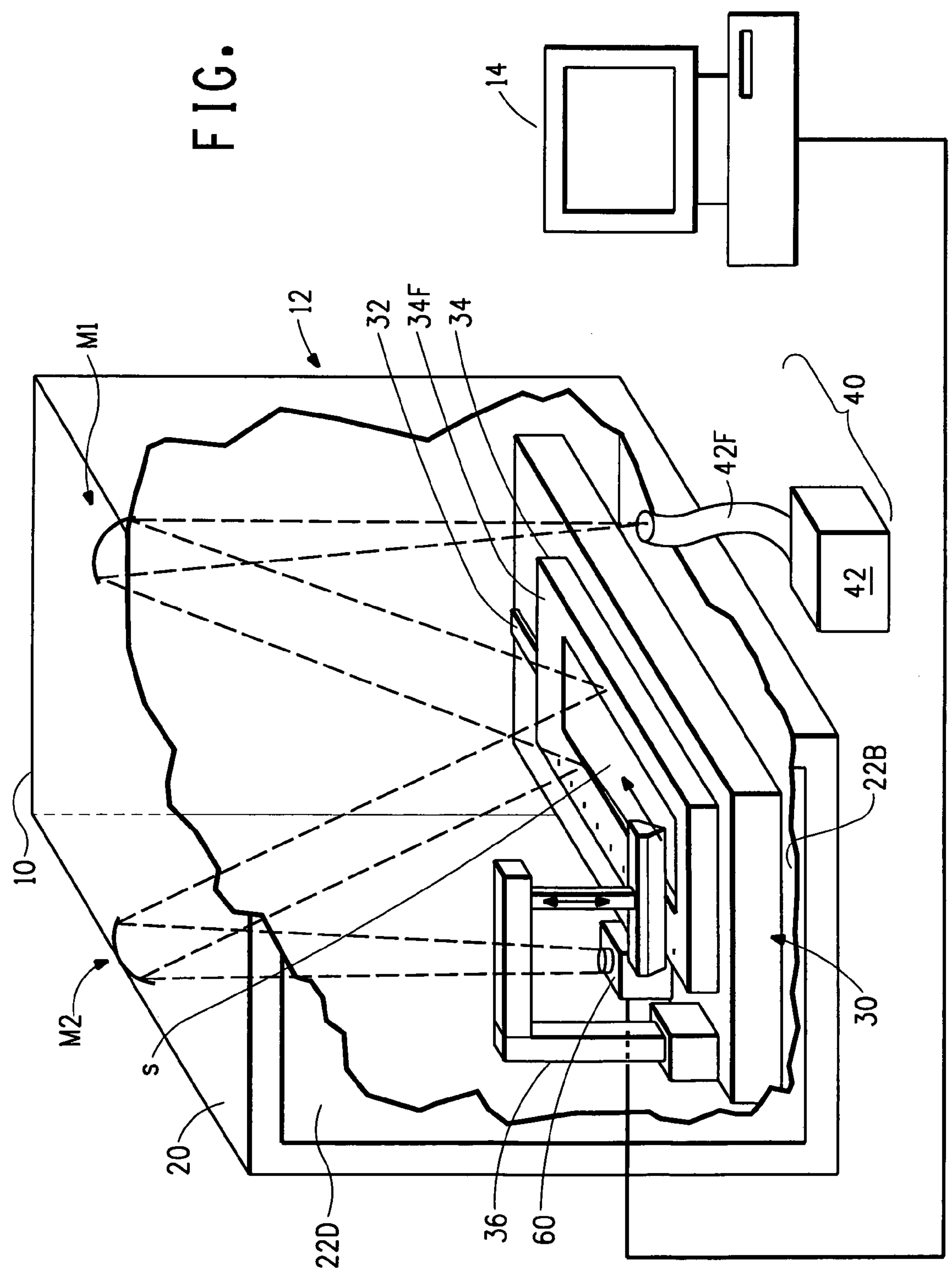
FIG. 1 is a pictorial view illustrating the components of the system.

The apparatus 10 of the present invention, as seen in FIG. 1, comprises an imaging assembly 12, also referred to as the sample imaging assembly, and an associated computerized image processor (or simply computer) 14. The sample imaging assembly 12, best seen in FIG. 2B, comprises a light-tight housing 20 in which are mounted a sample holding drawdown assembly 30, an illumination assembly 40 (see FIGS. 1 and 2A), and an image creation arrangement 50 (see FIG. 2A or 2B).

The housing 20 comprises a generally rectangular enclosure (best seen in FIG. 1) having side walls, a top wall, and a hinged door 22D a bottom wall 22B, upon which is mounted the sample holding drawdown assembly 30. The sample holding drawdown assembly 30 comprises a gage block holding device 32 that holds a four inch wide modified Hegman gage block 34, in which a sample S is placed, and a motorized drawdown mechanism 36. The flat top face 34F of the gage block 34 defines a sample plane. The drawdown mechanism 36 is a commercially available ADM-2 Automatic Drawdown Machine available from Little Joe Industries of Hillsborough, N.J., modified to receive the gage block holding device 32. The drawdown mechanism 36 is motor-driven, the speed being controllable by a speed control (not shown). The blade angle of the draw down mechanism is positioned at an angle to the plane of the block. The blade angle can be continuously adjustable or adjustable in increments, typically of one degree, and can be about 90 degrees or less with about 85 degrees being the preferred blade angle. The blade pressure is adjustable up to about 3.25 kilograms. The blade angle is sufficient for forming a film-like layer of the sample in the tapered path. The configuration of the blade and the blade angle can form a film-like layer which can be substantially flush with or slightly lower than the surface of the block.

Figure 2A:
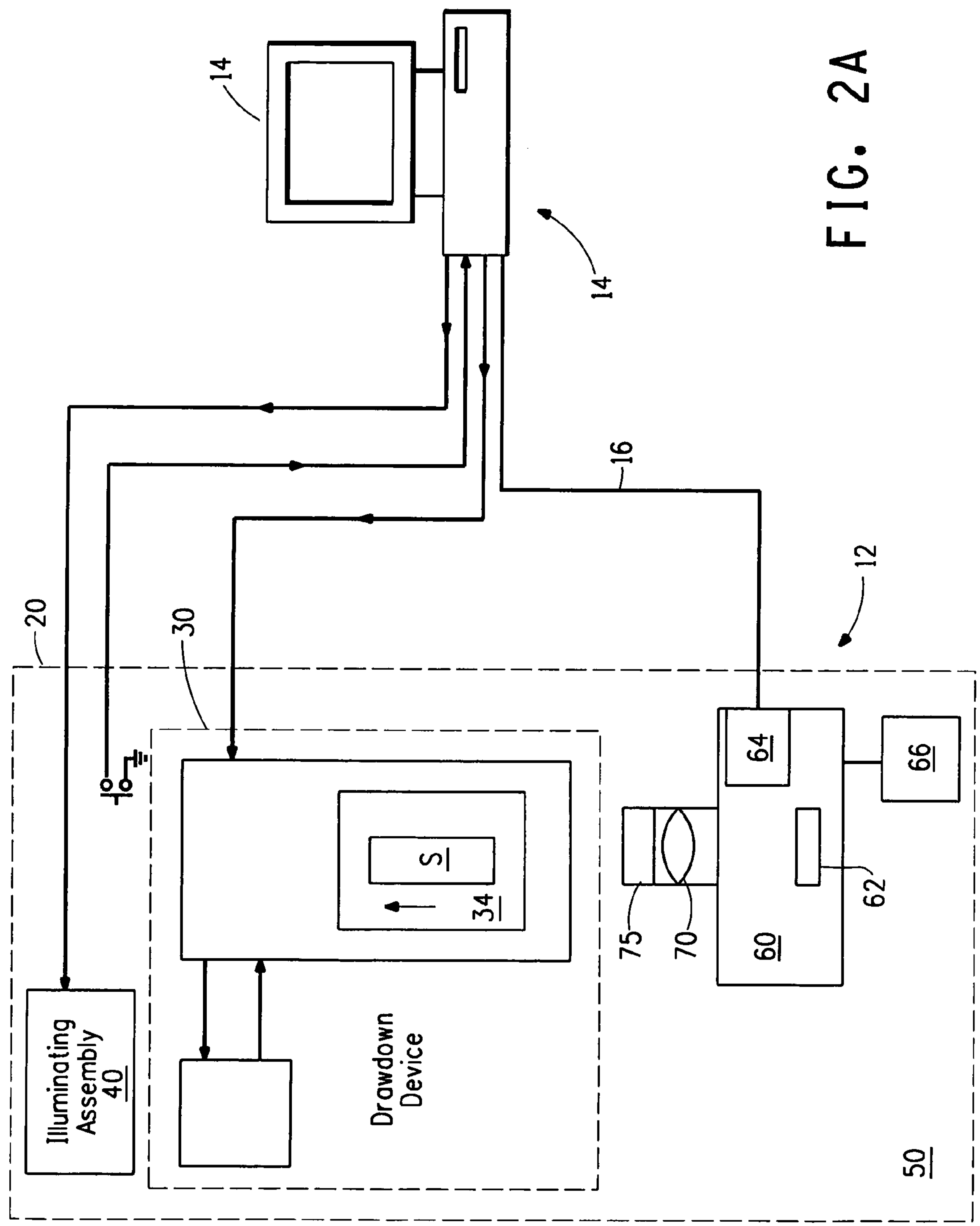
FIG. 2A is a block diagram showing the overall interconnection of the system components.

The illumination assembly 40, which illuminates the planar sample S, comprises a light source 42 and a fiber optic illuminator bundle 42F. The fiber optic illuminator bundle 42F is preferably a 1000-Micron Plastic Simplex PVC SMA/SMA, available as Part # EQ-7148.0, from Stonewall Cable, Inc., Rumney, N.H. The light source 42 is preferably a 20 volt, 150 watt halogen light source powered by a power source, such as a model DCR® III Plus, part # A20870.2, available from SCHOTT North America Inc. of Auburn, N.Y., which is controllable by the computerized image processor 14. The light source is run at a relatively low intensity level and is thus expected to have a long lifetime. Periodically, the light level is reset to account for a slow decrease in output over time The image creation arrangement 50 comprises a first spherical mirror M1, a second spherical mirror M2, a CCD camera 60, a photographic lens 70 and an optical filter assembly 75, the photographic lens 70 and optical filter assembly are shown in FIG. 2A.

The optical filter assembly 75 (see FIG. 2A) typically comprises a commercial haze filter mounted on the front of the lens 70 and the camera 60, and serves primarily to mechanically protect the lens 70 from possible splattering with sample material. If desired an optional filter assembly 80, shown in FIG. 2B, may be used to control the spectral response of the system so that the image analysis method utilizes information in a predetermined spectral region, such as to match the spectral response of the human eye.

The camera 60, such as a model KP-M1 video camera, available from Hitachi Denshi America, Ltd. of Woodbury, N.Y., has an associated camera power supply 66. The lens 70 can be a Nikon 35 millimeter focal length photographic lens. The camera 60, comprising a CCD photodetector array 62 and associated control and interface electronics 64, is mounted with the CCD photodetector array 62 positioned so that the sample plane is imaged by the second spherical mirror M2 and the lens 70 onto the CCD photodetector array 62. The photographic lens 70 is typically set with its aperture at about f/8. A field of view of about 10 centimeters by 13 centimeters (4.0 inch×6.0 inch) on the sample S is typically imaged.

Figure 2B:
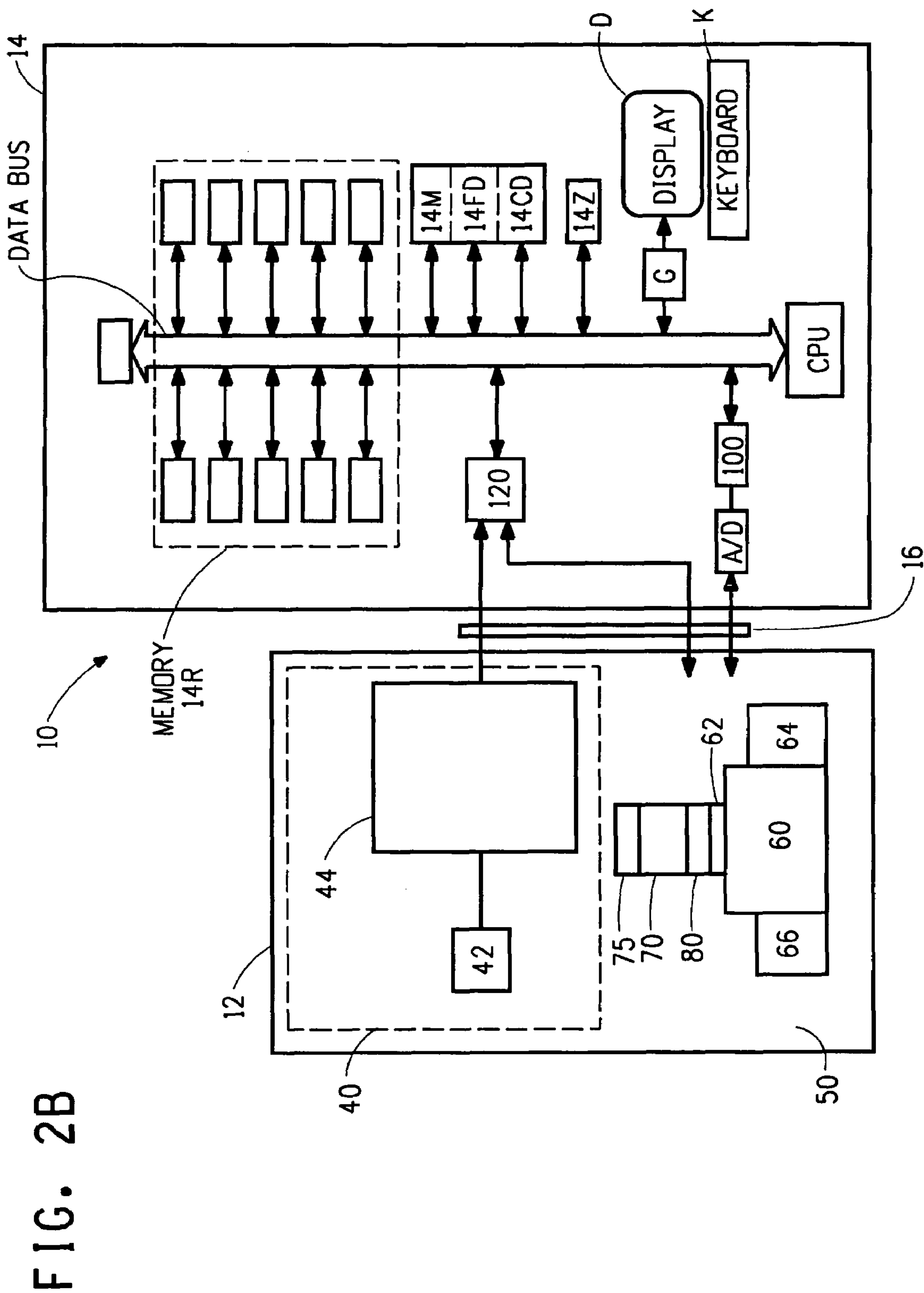
FIG. 2B is a block diagram showing a more detailed view of the system components and the components of the computer.

Referring to FIG. 2B, video images generated by the camera 60 are transmitted by a cable 16 to the computerized image processor 14. The computerized image processor 14 may comprise a Broadax Systems, Inc. (BSI) model PC-ATX-N9T12-15 Portable Computer. This computer comprises a display device D, such as a 15.4 inch TFT 1280×1024 LCD screen with analog-to-digital video signal converter; integrated keyboard with touch pad, built-in speakers, 300 Watt ATX power supply; two 5.25" vertical, two 3.5" horizontal open, one hidden 3.5" drive bays; and wheeled carrying bag w/retractable handle. Standard Configuration Includes an ATX motherboard, an Intel Pentium III 733 MHz CPU, Random Access Memory (RAM) 14R comprising 128 MB SDRAM, magnetic storage devices 14M comprising a 10 GB EIDE hard drive, a 1.44 MB floppy drive, a 48× EIDE CD-ROM drive, a graphics module G comprising an ATI 8 MB AGP SVGA card. Also included are a local area network module LAN, comprising a 3COM #3C905-TX 10/100BT LAN (PCI), an Iomega internal 250 MB Zip drive (EIDE) 14Z and operating system software such as Microsoft's Windows XP®. Peripheral devices include a National Instruments Corp. model PCI 1409 multi-channel monochrome frame grabber 100 (National part number 778200-1), model PCI 6503 digital I/O card 120 (National part number 777690-1), and associated software such as IMAQ Vision for Labview (part number 778044-1).

Sample Preparation and Hegman Gage

A pigment sample to be evaluated is dispersed in an alkyd resin. A sample volume of approximately 2 to 3 milliliters of the pigment/resin is deposited in the deep end of the tapered path on the Hegman gage block. The scraper bar draws down the pigment/resin, filling the tapered path on the Hegman gage with approximately 0.6 milliliters pigment/resin. The remaining pigment/resin is excess.

A modified Hegman Gage block having a 10 centimeter (four inch) wide tapered path can be used instead of the 1.25 centimeter wide path gage block described in ASTM Standard D1210. The modified gage block accommodates a sample about eight times as large as the ASTM gage block. The modified gage block 34 also has a mounting slot machined into the back of the gage block to facilitate mounting the gage block in the gage block holding device 32. The modified gage blocks are lighter since they are about ½ as thick as the ASTM Standard D1210 gage blocks and they are slotted on the bottom to fit into the gage block holding device associated with the motorized drawdown assembly. Other size Hegman Gage blocks could be substituted if desired.

The drawdown is done with the Hegman gage mounted inside the enclosure, with the drawdown and image acquisition being performed under control of the computer 14, to allow precise timing of the time interval between drawdown and image acquisition.

Calibration and Setup

Correlation of Image with Hegman Scale: With a Hegman Gage in place in the sample holder, a cursor line in the image is interactively aligned, in turn, with two predetermined lines on the Gage, e.g., gage marks at Hegman 7 and Hegman 2, to determine the equation that relates the image y-coordinate to the Hegman scale. This is done once at instrument setup.

Light Level calibration is done at instrument setup and at predetermined recommended time intervals (typically once a month) since the light source intensity is expected to decrease over time. Using a glass/epoxy calibration standard, a light level adjustment procedure in the software is run. This procedure automatically adjusts the light source voltage to give a predetermined average grey level in the region of interest of the image (i.e., the region of the paint film in the tapered path). A typical target average grey level is 200 (out of a 0 to 255 range). A binary search algorithm is used to arrive at the predetermined light level. Alternatively, instead of the glass/epoxy calibration standard, an actual drawdown paint film sample can be used to set the light level.

The detection algorithm used is substantially independent of light level, since it is based on contrast. It has been found that the image has to get noticeably dark before a low light level would affect the detection of agglomerates.

Video images, typically measuring 640 pixels wide by 480 pixels high, are digitized by an eight-bit (256 gray levels) analog to digital (A/D) converter in the frame grabber 100 and are stored in a suitable memory device. Camera voltage levels between 0 (pedestal level) and 0.714 are digitized to gray levels between 0 and 255.

Control of Illumination Level

The computerized image processor 14 is programmed to precisely control the light level illuminating the sample object S. This is accomplished by illuminating the surface of the sample object S with illumination assembly 40, with the light source being set to an initial output level. A digitized frame-averaged image of the surface is created by first imaging the light reflected from the surface onto the photodetector array to create an electrical signal representative of the image. The electrical signal is digitized and frame averaged a predetermined number of times and the frame-averaged representation of the image is stored in the image processor memory. The average gray level in the image is determined and the illumination level of the sample object S is adjusted until the average gray level in the image is at a desired level, typically near a value of 200 as previously described.

Dark Current or Dark-Reference Image

A dark-reference image is acquired with the light source turned off. This image is stored and subsequently subtracted on a pixel-by-pixel basis from each sample image to remove the effects of dark current in the CCD array of the camera. The dark-reference is acquired at program startup and then it is automatically acquired periodically at a predetermined time interval, e.g., every 2 hours. If the enclosure door is open when a reference needs to be acquired, the computer system 14 will generate a prompt which is displayed on the screen for the operator to close the door.

General Description of the Optical System

Figure 3:
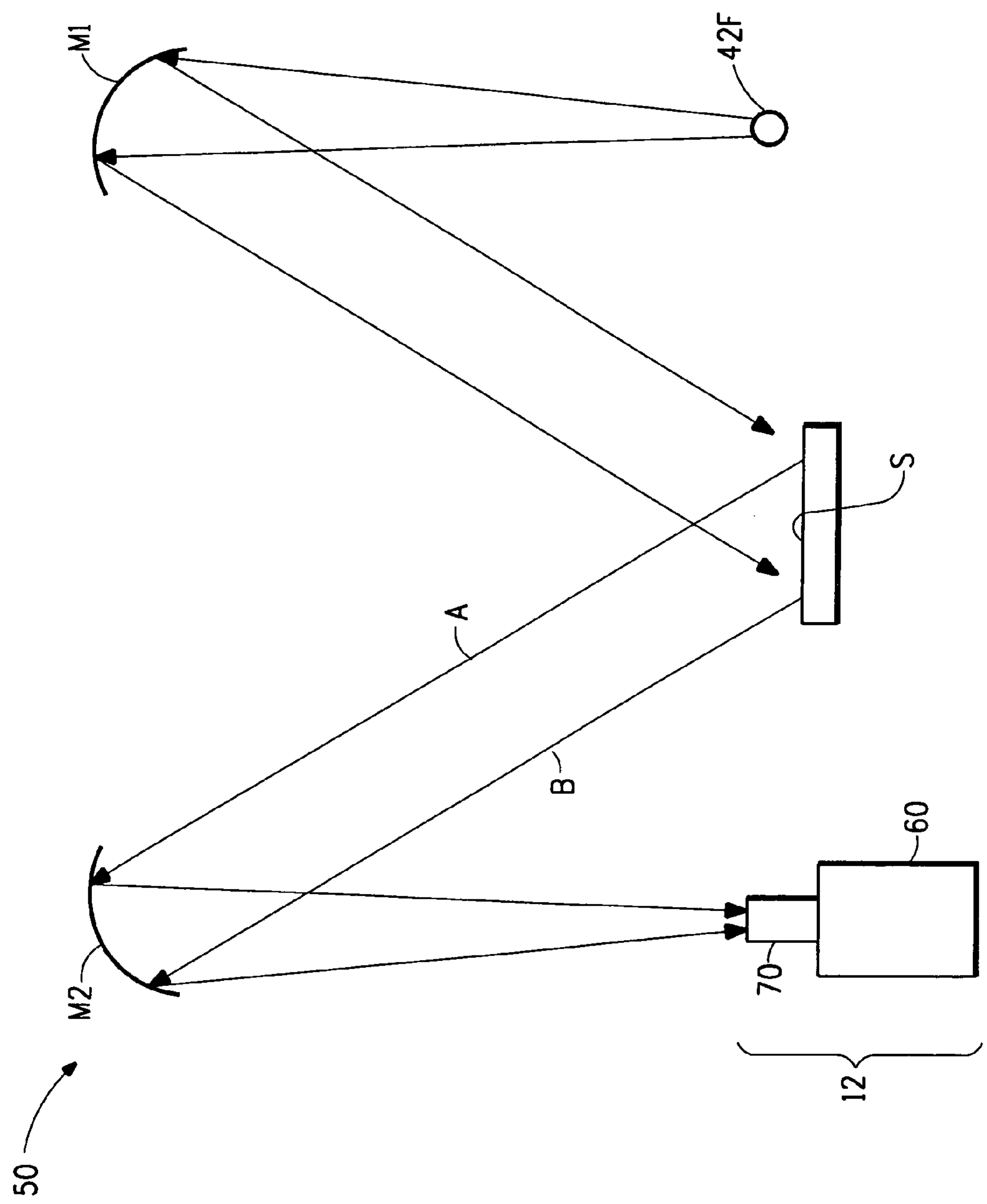
FIG. 3 is a sectional view showing the arrangement of the optical components of the system.

A sectional view of the optical system is shown in FIG. 3. A source of light from the fiber-optic illuminator bundle 42F and a first spherical mirror M1 are used to illuminate the sample S. A second spherical mirror M2 and a camera 60, having an associated lens 70 form an image of the sample plane on the CCD detector 62 (see FIGS. 2A and 2B). The illumination assembly 40 comprising the light source 42 and the fiber-optic illuminator bundle 42F, shown in FIG. 1, is used for safety. The light source 42 is positioned outside the enclosure 20 to avoid potential safety issues related to flammable volatile vapors from the sample or from cleaning solvent used to clean the gage block.

Light is directed from the end of the fiber-optic illuminator bundle 42F to a first spherical mirror M1. The first mirror M1 is located approximately one focal length (about 24 inches) from the output end of the fiber-optic light guide 42F so that light reflected from the mirror M1 is directed in a substantially collimated manner to the sample surface S to be imaged. A second spherical mirror M2, located approximately one focal length (about 24 inches) from the lens 70 collects the light reflected from the sample S and directs it to the camera 60, thereby focusing an image of the fiber-optic light guide 42F onto the aperture stop of lens 70. This arrangement defines a "bright field" imaging arrangement.

The sample surface S to be imaged is located on the modified Hegman gage block 34. The area of the sample to be imaged is approximately 4-inches wide (left to right in FIG. 2A) and 6-inches long (top to bottom in FIG. 2B).

Sample Imaging: The spherical mirror M2 and the lens 70 are used to form an image of the sample S onto the detector 62 of the camera 60. Since the second mirror M2 is approximately one focal length (24 inches) from the sample plane, it forms a virtual image of the sample plane. The lens 70 then focuses this virtual image onto the CCD photodetector array 62.

As shown in FIG. 3, in the absence of any protruding particles on the sample surface, a uniformly illuminated image of the sample surface is obtained. Light rays A and B (illustrated by arrows) strike the paint surface where there are no particles and a substantial portion of the light intensity in these rays A and B is specularly reflected toward mirror M2. Mirror M2 forms a virtual image of the surface and this virtual image is collected by the lens 70 and projected onto the photodetector array 62, resulting in relatively bright image areas corresponding to the locations on the sample where the rays were incident.

Figure 4:
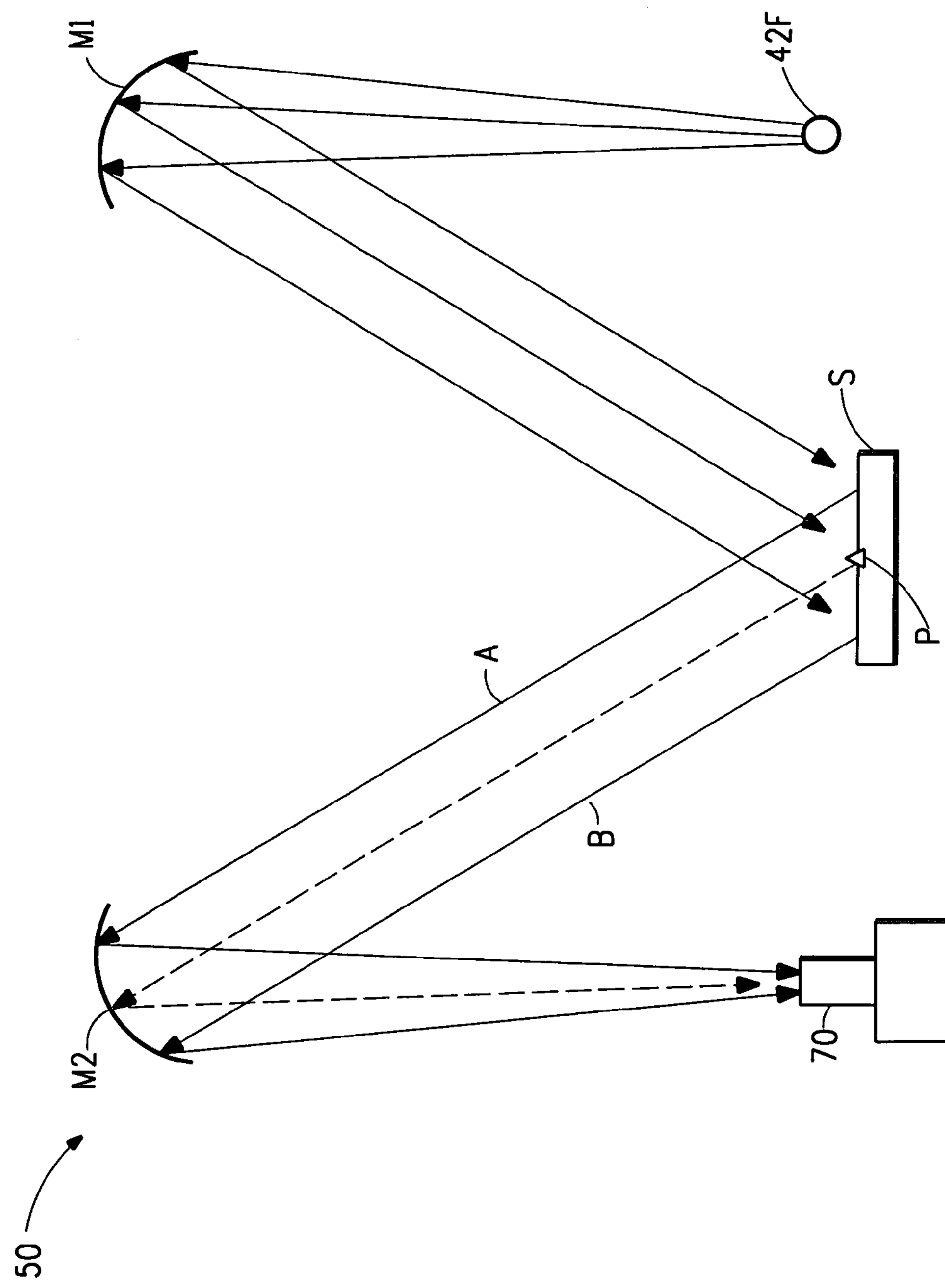
FIG. 4 is a sectional view showing the interaction of light rays with the surface of a sample.

As shown in FIG. 3, a particle P on the surface of the sample S diverts light away from mirror M2, substantially reducing the portion of the light intensity in ray C that is specularly reflected toward mirror M2, collected by the lens 70 and imaged onto the photodetector array 62. This results in a relatively dark spot in the image projected onto the photodetector array 62 corresponding to the location of the particle P. As shown schematically in FIG. 4, ray C strikes a particle P that is protruding from the surface of the sample and this light is diverted in several directions. Only a small fraction of the light energy from ray C reaches mirror M2, so the image position corresponding to the location of the particle is relatively dark compared to the image positions corresponding to particle-free areas of the sample surface. It should be noted that a similar effect would be obtained for a surface depression.

Figure 5:
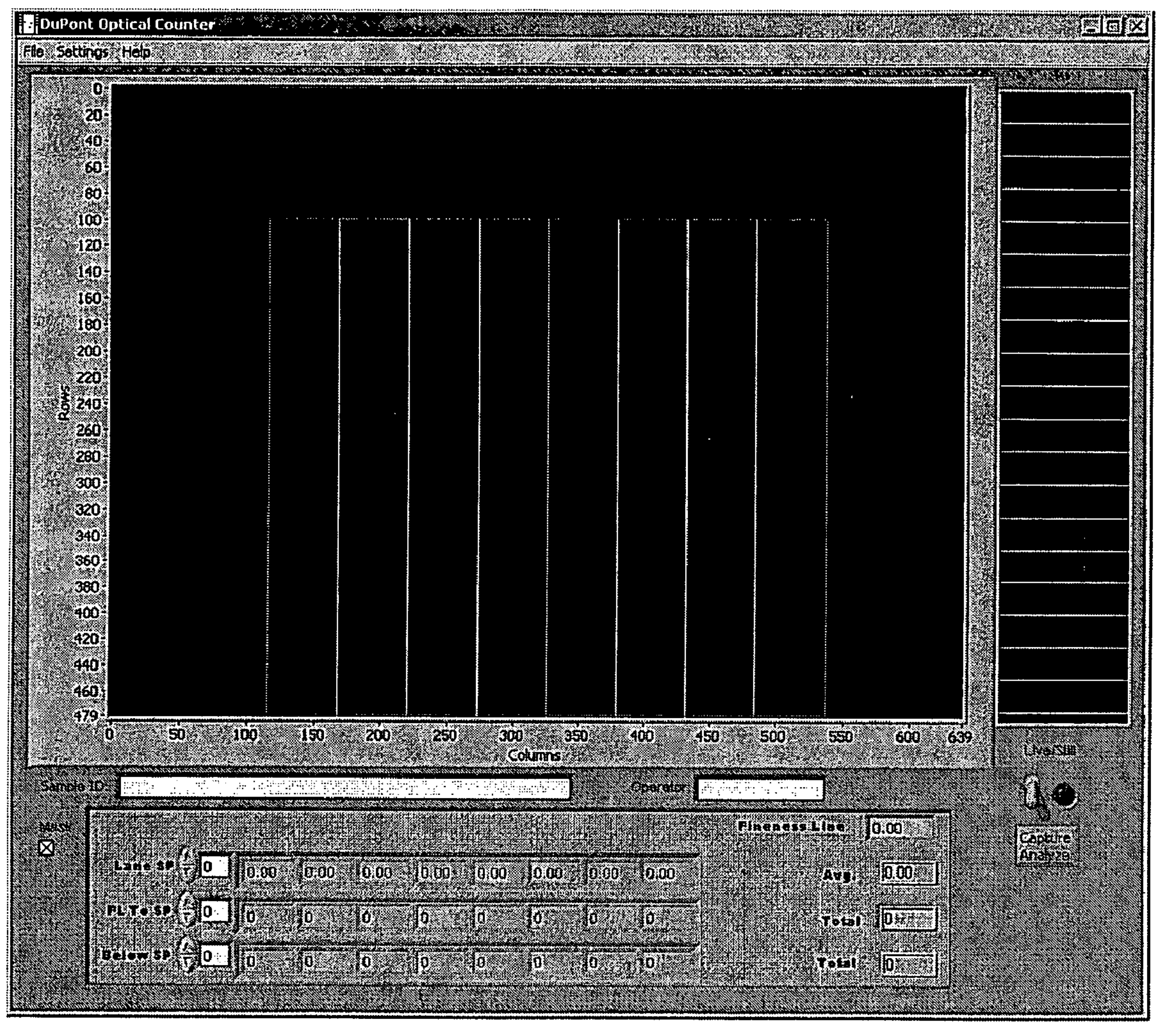
FIG. 5 is a view showing the initial display of a blank image on the computer screen.

Image Window At startup, as seen in FIG. 5, the Image Window displays a blank image and empty data fields. The box with the vertical lines represents the area of measurement, i.e., the area of interest on the Hegman Gage, and the vertical lines show the boundaries of the eight channels used for analysis.

A program toggle switch (labeled Live/Still) is provided that allows the user to switch between a live video image (upper toggle position) and a still image (lower toggle position). A live image is continually updated with new image information; a still image is fixed. In going from Live to Still, the program does a video frame average and adjustment using the reference image. A live image mode is indicated also by a green indicator light.

To facilitate documenting the collected data, a Sample ID and Operator name must be entered before any measurement can be done. The Sample ID is used as the root name of the data file where the measurements are saved. If the Sample ID and Operator fields are blank, the Capture/Analyze button (and Analyze Current button, described below) is grayed out, indicating that these functions are disabled.

Figure 6:
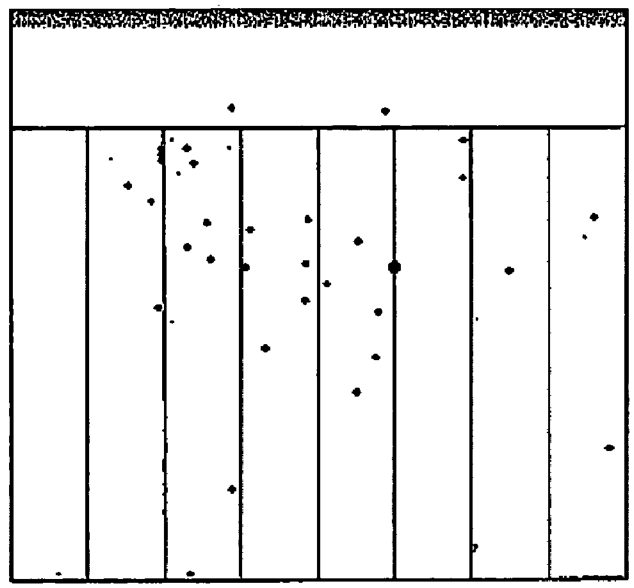
FIG. 6 is a view showing an image of a sample displayed on the computer screen.

In the image of FIG. 6, a Hegman Gage calibration standard is in place on the sample holder. Live images are color coded. Typically pixels in a live image that represent image locations where there is saturation (i.e., the highest possible gray level) are displayed in the color red. In the image of FIG. 6, this occurs on the bare metal areas of the Gage (the darker area along the top). Since only the region of interest shown by the cursor box (with the eight channels) is analyzed, the saturation outside this region is of no consequence. A "Mask" checkbox is provided. If this checkbox is checked, then only that part of the video image that is inside the area of measurement is displayed, as is displayed in FIG. 6.

Image Analysis

Basic Particle Detection Algorithm: The detection of a particle is based on its local contrast level, that is, the relative grey level of the particle compared with its local neighborhood. As a result of the optical system used, particles appear as dark spots against a relatively light background as in the example image of FIG. 6.

The image is oriented such that higher Hegman values (i.e., the shallower portion of the tapered path) are at the top of the image and lower Hegman values (deeper portions of the tapered path) are at the bottom of the image. The drawdown is done in the direction from the bottom to the top of the image.

A region of interest is selected at instrument setup. Typically, it is defined by the area between Hegman value 7 and Hegman value 2 and the across the width of the tapered path in the gage block. The analysis takes place only within this region of interest. Two parameters, S1 (side dimension of square that defines the local neighborhood) and S2 (Sensitivity Factor), are used to control the detection algorithm as the region of interest is examined one pixel at a time in a raster-scanning manner.

Figure 7:
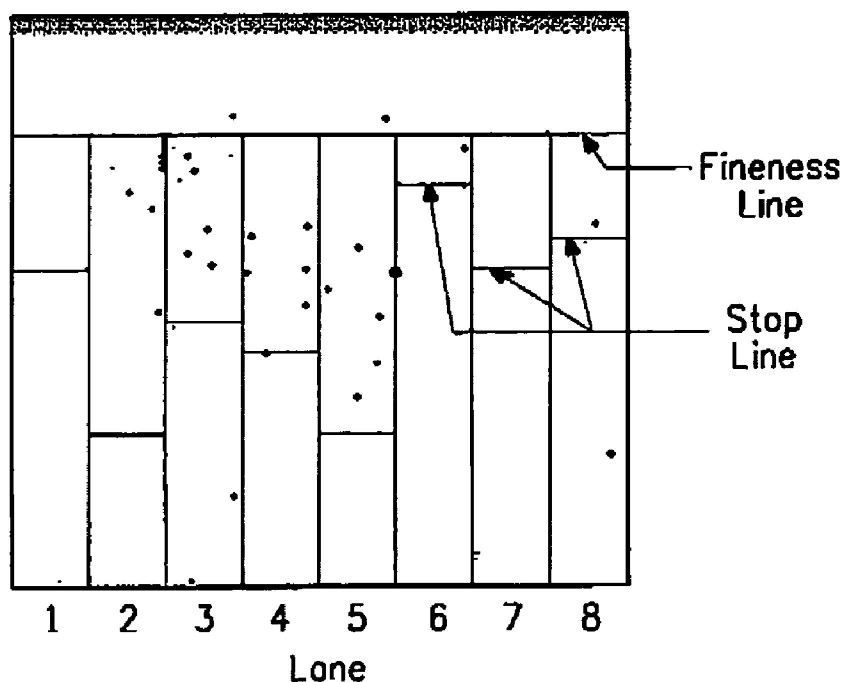
FIG. 7 is a view showing the display of an analyzed image on the computer screen showing the detected agglomerates, the fineness line, and the stop point along each lane on the sample.
Figure 8:
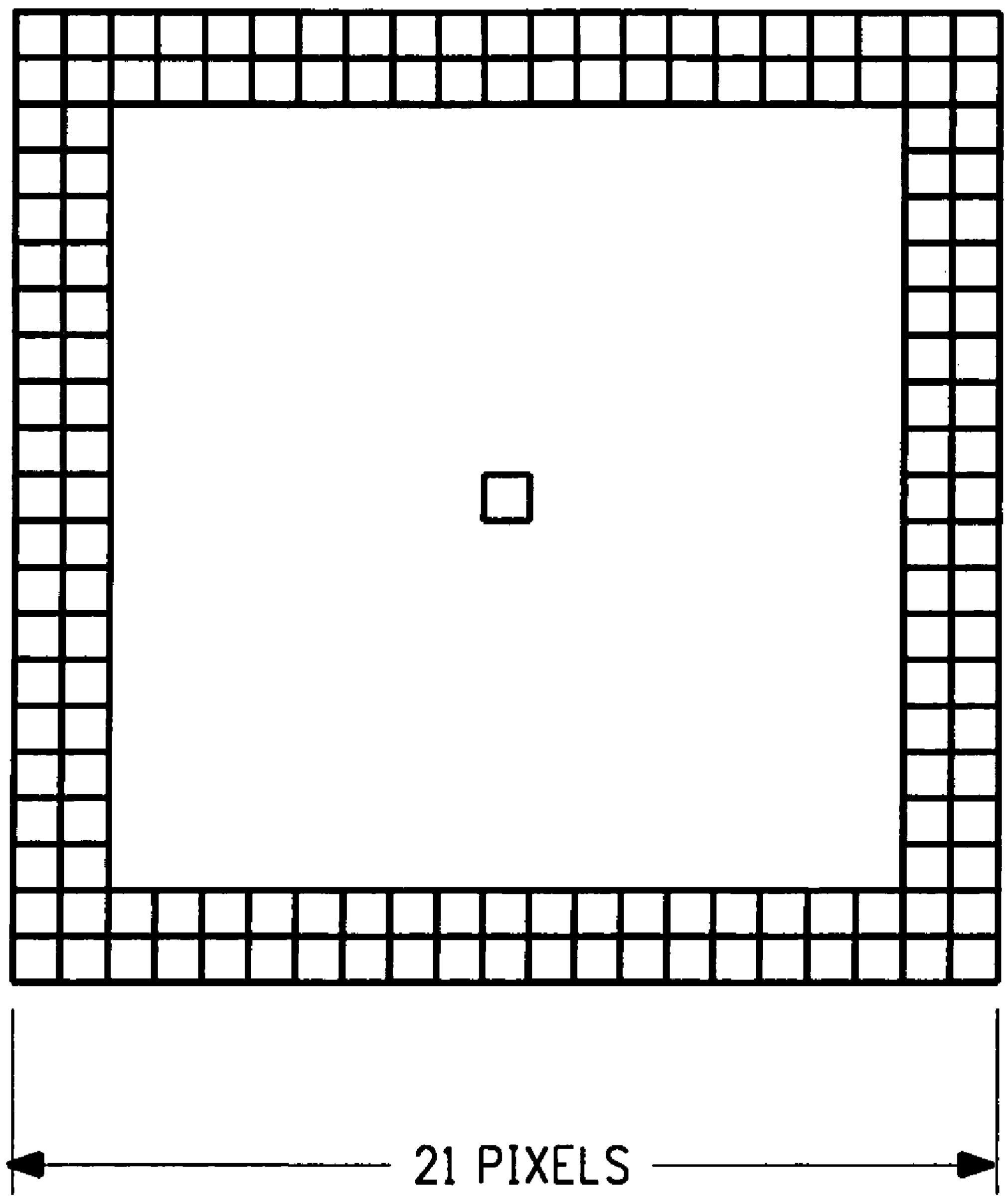
FIG. 8 shows a pixel of interest, surrounded by the adjacent pixels used to calculate the local average grey level for the contrast ratio determination.

At each pixel, a square local neighborhood area is constructed, centered on the pixel. The length of a side of the square, S1, in pixels, is specified. Typically, S1 is set to a value of 21. The average grey level G, of the pixels along a perimeter area of the square is first determined. Referring to FIG. 7, a 2-pixel wide perimeter surrounding the pixel of interest is used to calculate the average grey level G. Thus the perimeter has an outer side length of S1 pixels and an inner side length of (S1−2) pixels.

The Sensitivity Factor S2, expressed as a percentage, is selected. Typically, S2 is set to a value of 50 percent. If the grey level of the center pixel is less than the S2 percentage of this average grey level G, then the center pixel is considered part of a particle. That is, the condition for particle detection is:

$$\text{Center pixel grey level} < S2 * G/100$$

It has been found to be important not to sample the full internal area of the local neighborhood square to calculate average grey level G. If the particle size dimension approaches the value of S1, then the particle itself could unduly influence the value of G, thus preventing detection of all of the pixels inside the particle. If desired, a different neighborhood can be used, for example a 3-pixel wide square.

It should be appreciated that if the density of scats is high, then the presence of other particles within the square local neighborhood will affect the calculated average grey level G. In such an instance other particle detection criteria may be used to analyze densely populated images. For example, in place of the calculated average grey level G, either a maximum grey level or a suitably defined average of the higher-valued grey levels may be used.

To display the results of the particle detection image analysis a separate, auxiliary image array is created that initially has all pixels set to a grey level zero (0) (OFF). If a pixel in the sample image meets the above detection criterion as a particle, then its corresponding (i.e., same location) pixel in the auxiliary image array is set to a fixed value, say 255 (ON).

After the region of interest in the sample image has been analyzed, the binary auxiliary image created will contain regions of contiguous pixels set to the ON value. Each of these regions of contiguous pixels corresponds to a specific particle in the sample image. This auxiliary binary image may be traced, using standard binary image tracing methods, to locate each of the particles as separate objects. In the original sample image, the regions that have been determined to be particles are then highlighted, e.g. in red, for visual feedback to the operator.

The number of pigment agglomerates or particles that protrude from the paint surface (called scats) between the Fineness Line and the Stop Point (as will be defined) are automatically determined. If the Fineness Line is above a Hegman value of 7, the scat count is done between Hegman 7 and the Stop Point. If the Fineness Line is below Hegman 7, the scat count is done between the Fineness Line and the Stop Point.

Figure 9:
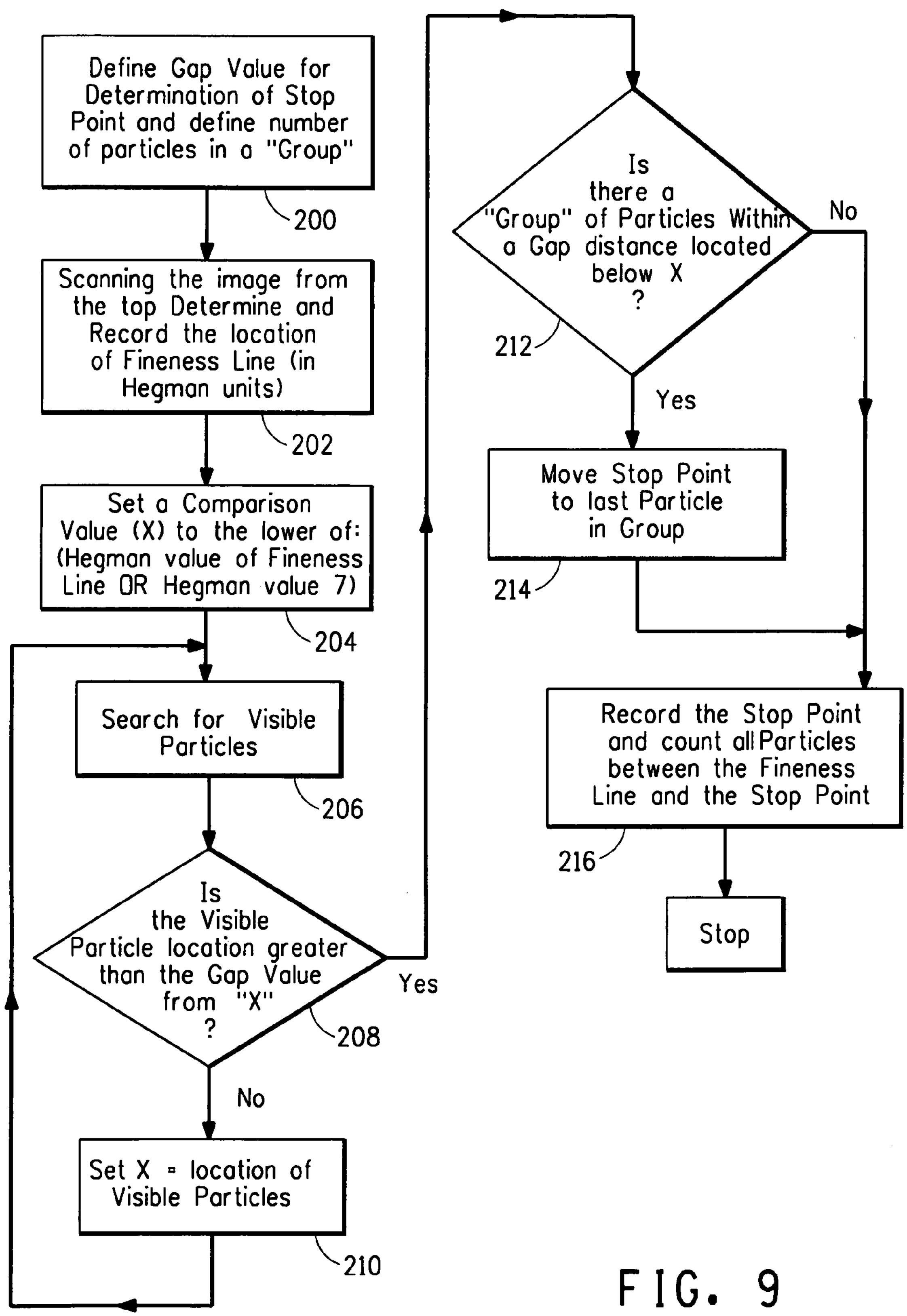
FIG. 9 is a block diagram showing the method used to determine the Stop Point.
Figure 10:
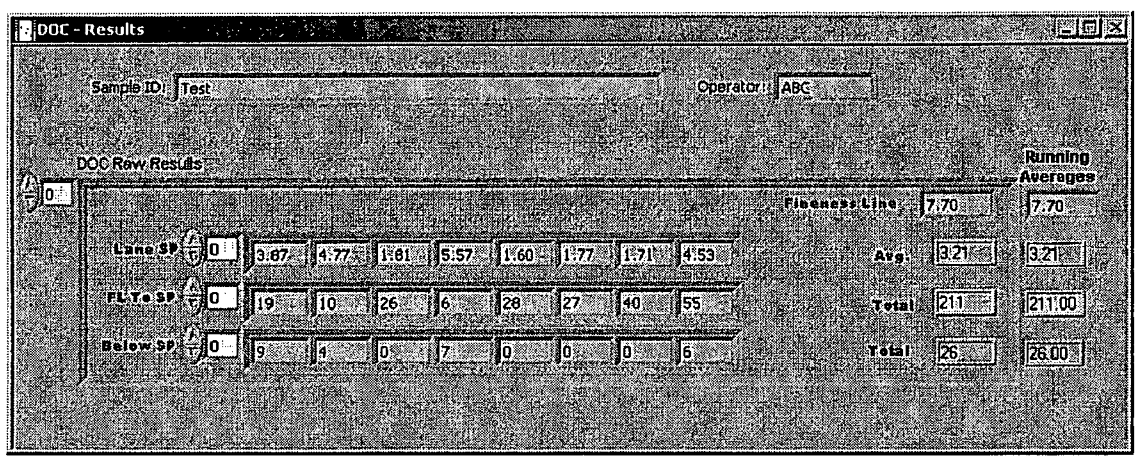
FIG. 10 shows a display of numerical results from an analyzed image of a sample.
Figure 11:
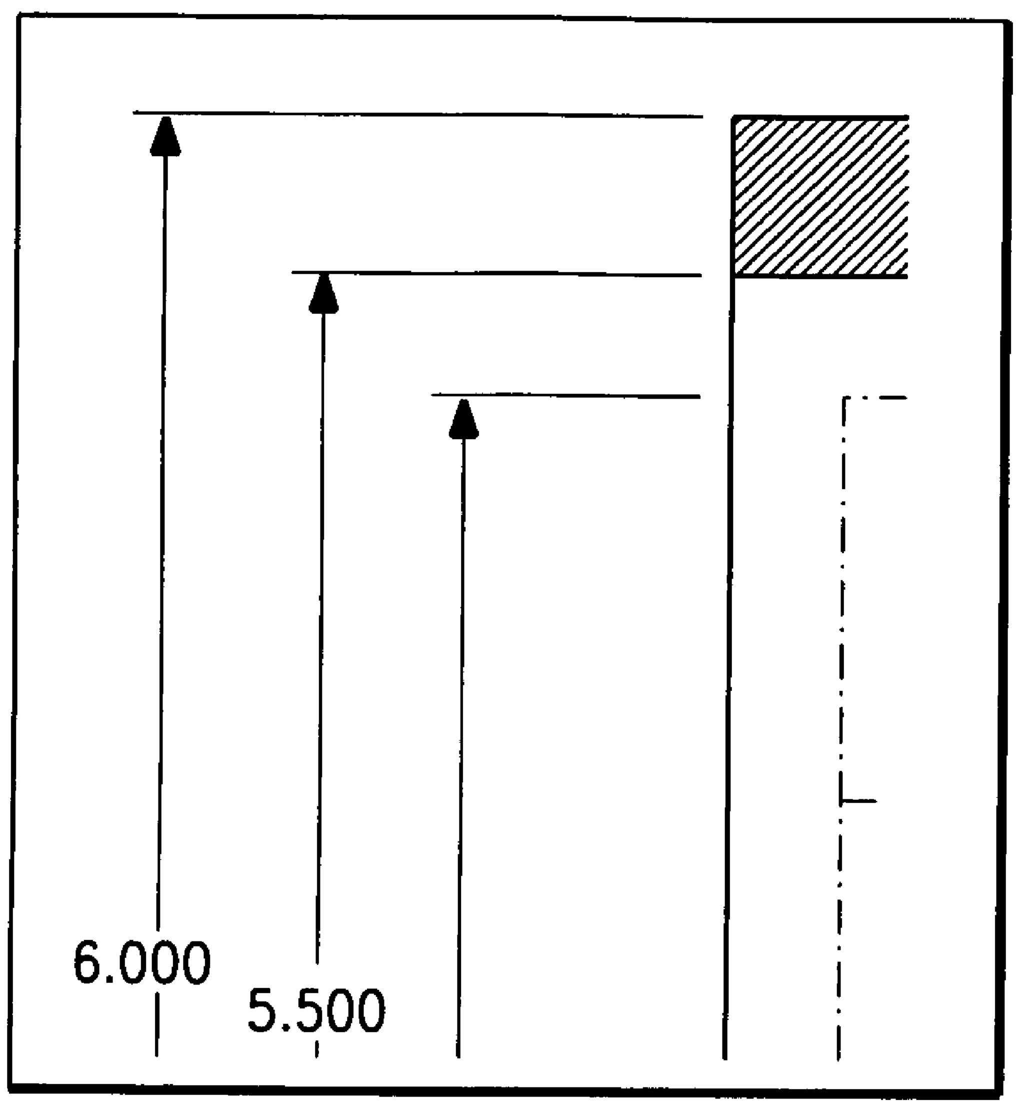
FIG. 11 shows the details of a calibration standard that simulates a drawdown sample.

Determination of Stop Point: The region of interest, i.e., the area of the image corresponding to the tapered path, is typically divided into eight parallel channels, each corresponding to a half-inch wide portion of the tapered path. Reference is now made to FIG. 9, which shows a flow chart of the method of determining the Stop Point within each of these channels. For purposes of locating the Stop Point, a size Gap is defined by parameters in the software as some fraction of a Hegman gage unit, typically about one unit (block 200). For example the Gap might be 80% of a Hegman unit or it could be 120% of a Hegman unit. The image is scanned and the Fineness Line is first determined (block 202). The Fineness Line is the line in the image above which the concentration of visible particles begins to increase rapidly from at least four particles in a horizontal line in a given channel in the image. A Comparison Value X is set to the lower of the Hegman Value of the Fineness Line or a Hegman Value 7 (block 204). Scanning each channel of the image in a downward direction to search for Visible Particles (block 206), the Comparison Value X is set equal to the location of a Visible Particle (block 210). initially located at the Hegman unit corresponding to the last particle found before the defined Gap (i.e., defined fraction of a Hegman gage unit in the field of particles below the Fineness Line). However, if there is a "Group" (typically set to at least three or more particles) below this gap (block 212), the "Group" being vertically spaced within the defined Gap, then the Stop Point will be relocated to the Hegman value of the last particle found in the group (block 214). The scanning of the image continues until no more groups of three or more particles are found. The number of particles between the Fineness Line and the Stop Point are then counted to determine the number of detected scats (block 216).

Alternate Method of Determining the Fineness Line: If desired an alternate method may be used to determine the Fineness Line. The region of the image starting at Hegman value 7.5 through Hegman value 2 is run through the scat analysis. A sensitivity value separate from that used for normal scats tracing is employed. A parameter that limits the height and width of detected object is used. Here only very small scats are of interest. The Y coordinate of each detected scat is captured and totals for each line of the image from top to bottom are calculated.

The gage is divided into regions depending on the binning resolution chosen. Typical binning is ½, ¼ or ⅛ Hegman units. For instance all the scats from just above 7.25 to 7.5 are considered in the 7.5 binning (using ¼ Hegman binning). The totals for each bin are calculated and then divided by 8 to provide an average lane count.

The count data is fitted to a curve to smooth the counts from bin to bin. The curve values are then compared to a threshold. Once the counts fall below the threshold the bin containing less than the threshold will be considered where the Fineness Line occurs.

A software program in the computer 14 permits images to be captured and then automatically calculates the Fineness Line based upon the following parameters:

Sensitivity, Side of Square, ROI (all in one control)

Threshold

Cut off (largest object to be considered in count).

Binning (½, ¼ or ⅛ Hegman unit).

The settings below have been found to produce satisfactory results

| Bin | Cut Off | Threshold | Sensitivity |
|---|---|---|---|
| ⅛ | 2 | 5 | 70 |
| ¼ | 2 | 10 | 70 |
| ½ | 2 | 16 | 70 |

Data Output

The particle count in each of the eight channels and the total particle count are reported. Each particle that is reported has a Hegman value associated with it that reports the position of the particle (remembering that the position determines the approximate dimension of the particle). For a particle that consists of more than one contiguous pixel, the pixel that corresponds to the lowest Hegman value associated with the particle is used to define the particle's position and for calculating a Stop Point. Thus, if there is a streak in the image due to a particle being dragged and the streak is detected as a single particle, then the lowest Hegman value along the streak is used to define the particle location. This is done since streaks in the image are typically caused by a particle that is larger than the path depth being dragged along the path by the scraper blade.

The particle location along the Hegman Gage is used for the calculation of Stop Points. The particle location information is stored in memory and is available, if desired, for reporting the particle size distribution, e.g., the number of particles in each predetermined Hegman Gage interval.

Shape Factor: A Shape Factor is calculated to determine the aspect ratio of detected scats. The scat contour coordinates are examined and the minimum x-value (xmin) and maximum x-value (xmax) and the minimum y-value (ymin) and maximum y-value (ymax) are determined for each scat. A ratio of the y-dimension to the x-dimension (ymax−ymin)/(xmax−xmin) is calculated, which is termed the "shape factor". It should be noted that the pixels with xmax and xmin needn't be on the same horizontal line and the pixels with ymax and ymin needn't be on the same vertical line. The experienced practitioner will appreciate that other methods of streak detection can be used.

This shape parameter is sufficient for discriminating against the specific streak features that can be encountered when pigment agglomerates are dragged by the scraper. For such streaks the Shape Factor would be very large. A predetermined Shape Factor threshold is used to discriminate against streaks. A typical threshold value of 6 is used. Thus all particles with Shape Factor less than or equal to 6 are counted and particles having a higher value Shape Factor are not counted. Thus streaks can be discriminated out of the count if desired.

Operation of the System

Reference Image: When the software program starts, a dark-reference image is automatically taken. A microswitch is used to insure that the door to the enclosure is closed to prevent stray light from entering the enclosure and to enable dark-reference image acquisition. If the door is not closed, the acquisition of a dark-reference image is disabled and the operator is prompted with a message window on the computer display. When the door is closed, this message window is removed and acquisition of the dark-reference image is re-enabled.

During dark-reference image acquisition, a message window appears signaling that a frame average is taking place. This means that a large number of video frames are being averaged to reduce noise in the reference image. The same frame averaging is used for all sample images to improve the reproducibility of the measurements.

Dark-reference images are acquired periodically during program operation at predetermined time intervals. When the program has determined that it is time for a dark-reference image to be acquired, the operator is prompted with a message window on the computer display instructing the operator to close the door of the enclosure.

The operator places the Hegman Gage on the holder. The operator then closes the door to the enclosure and signals the drawdown unit to begin a drawdown. As the drawdown is done, the scraper blade moves along the Gage block, creating a sample of the pigment dispersion in the tapered path. The computer counts a delay time from the start of the drawdown to determine when the image of the sample is acquired. A switch is located at the door of the instrument to confirm that the door is shut when a drawdown begins or when a dark-reference image is taken.

In order to periodically confirm instrument operation, a Gage with a reference sample is used as a calibration standard. The calibration standard comprises a metal plate, with an undersurface mounting arrangement the same as the Hegman Gage block, having a sheet of one-eighth inch (about three millimeter) thick float glass mounted on its upper surface. The bottom surface of the float glass is painted white. The top surface of the float glass has small, randomly placed drops of epoxy. When imaged in the apparatus of the present invention, the drops show up dark against a bright background and are detected/analyzed as if they were scats in a pigment dispersion sample drawdown. The calibration standard serves as a fixed sample, whose readings are known, for periodically checking the operation of the unit. The one end of the top surface corresponding to the shallow end of the tapered path (the end that is at the top of the image) has a frosted band across it to provide a visual feature for the Fineness Line algorithm to use.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In one embodiment, the invention herein can be construed as excluding any element or process step that does not materially affect the basic and novel characteristics of the composition or process. Additionally, the invention can be construed as excluding any element or process step not specified herein.

Those skilled in the art, having the benefit of the teachings of the present invention as hereinabove set forth may effect modifications thereto. Such modifications are to be construed as lying within the contemplation of the present invention, as defined by the appended claims.

What is claimed is:

1. An automated computer-controlled method for measuring the quality of a pigment dispersion, the pigment dispersion being prepared by: i) combining a suitable resin with the pigment to be measured to form a paint or paste; and ii)

depositing a quantity of the paint or paste at a deep end of a tapered path of a Hegman gage block in sufficient quantity to substantially fill the tapered path, the method comprising:

a) placing the Hegman gage block in a holder in a motorized drawdown device, the holder sensing the presence of the gage block and signaling the computer that the gage block is present;

b) activating the motorized drawdown device to lower a scraper onto the Hegman gage block and drawing the scraper along the length of the tapered path at an angle to the plane of the block and at a contact pressure sufficient to form a tapered film sample whose thickness tapers from a maximum thickness of over one hundred microns to a minimum thickness of zero;

c) waiting a time interval;

d) arranging a light source, a first spherical mirror, the sample, a second spherical mirror, a lens, and a camera having a two-dimensional photodetector array, in a bright field arrangement, so that the light source and the first spherical mirror are capable of illuminating the sample in a substantially collimated manner at a light intensity level sufficient to reflect light rays from the sample to the second spherical mirror whereby the second spherical mirror is capable of directing the light rays to the lens of the camera;

e) acquiring an image of the sample with the two-dimensional photodetector array of the camera;

f) digitizing and storing the image in a memory in the computer; and g) analyzing the image within a region of interest corresponding to the tapered film sample along the tapered path to detect and count agglomerates in the pigment that protrude above the surface of the sample.

2. The method of claim 1 wherein step d) further comprises:

1) creating a calibration image of a calibration standard by illuminating the calibration standard with the substantially collimated light source, 2) capturing an image of the calibration standard, 3) calculating the average grey level of the image, and 4) adjusting the intensity of the light source so that the average gray level is within a range, thereby establishing a light intensity level sufficient to illuminate the sample.

3. The method of claim 1 further comprising creating a frame-averaged dark current image representing the response of the photodetector array in the absence of light; and storing the frame-averaged dark current image in the computer memory.

4. The method of claim 1, wherein the step (e) of acquiring the image of the sample further comprises:

1) collecting the light reflected from the surface of the sample with the second spherical mirror and directing the collected light to a lens;

2) using the lens to project an image of the sample surface onto a two-dimensional photodetector array to create an electrical signal representative of the image;

4) digitizing the electrical signal using an analog to digital converter;

5) frame averaging the electrical signal;

6) storing the frame-averaged digitized representation of the image as an array of picture elements in a computer memory;

7) creating a dark-current-corrected frame-averaged image by subtracting the frame-averaged dark-current image from the frame-averaged image of the sample on a pixel by pixel basis.

5. The method of claim 1, wherein step g) of analyzing the image further comprises:

1) for each pixel within the region of interest, that pixel having a pixel intensity, determining an average grey level of a first number of pixels surrounding that pixel, 2) calculating a ratio of the pixel intensity to the average grey level; and 3) comparing the ratio to a threshold to detect one or more contiguous pixels that represent agglomerates in the pigment that protrude above the surface of the sample.

6. The method of claim 5, wherein the first number of pixels surrounding that pixel excludes a second, smaller, number of pixels immediately adjacent to that pixel.

7. The method of claim 5, further comprising;

h) tracing the contiguous detected pixels of step g) to identify discrete agglomerates;

i) determining the position of each identified discrete agglomerate along a plurality of parallel channels along the tapered path of the Hegman gage block;

j) reporting the position of each identified discrete agglomerate in a visual display.

8. The method of claim 2, wherein the calibration standard is comprised of a reflectance standard.

9. The method of claim 2, wherein the calibration standard is comprised of a glass sheet in the shape of the Hegman gage block, the glass sheet having a back surface painted white to optically simulate the surface of a pigment dispersion sample and a front surface having a plurality of epoxy droplets thereon, the droplets optically simulating pigment agglomerates protruding from the pigment dispersion sample.

10. An apparatus for measuring the quality of a pigment dispersion, the apparatus comprising:

a) a light-tight enclosure comprising a sample holder, an illuminating assembly for illuminating the sample with substantially collimated light at an intensity level, and an imaging assembly, b) a computerized image processing assembly for controlling the illumination level of the sample by the illuminating assembly and for receiving images created by the imaging assembly and analyzing those images, wherein:

(1) the sample holder comprises a support frame, a Hegman gage block drawdown assembly for holding the sample to be measured in a plane and a motorized drawdown mechanism, (2) the illuminating assembly comprises:

i) a source of light, a reflector, and a fiber optic light bundle, the reflector reflecting light from the light source to an end of the fiber optic bundle proximal to the light source and the distal end being positioned to project light in a first direction;

ii) a first spherical mirror having a first focal length, the mirror being positioned about one focal length from the distal end of the fiber optic bundle and oriented to receive the light from the fiber optic bundle and to reflect the light to illuminate the sample with a beam of substantially collimated light; and (3) the imaging assembly comprises:

(i) a second spherical mirror,

Ii) a lens having a stop, iii) a two-dimensional photodetector array, and iv) a computerized image processing assembly, the second spherical mirror having a second focal length, the second spherical mirror being positioned one focal length from the lens and oriented to receive light directly reflected from the sample and to focus the light from the sample onto the stop of the lens;

the lens focusing an image of the sample onto the two-dimensional photodetector array, each photodetector in the array creating an electrical signal representative of the light reflected from a respective location on the surface of the sample, the photodetector array being electrically connected to the computerized image processing assembly, the electrical signal from each photodetector being transmitted to the computerized image processing assembly, the amplitude of the signal being digitized and stored in a memory as a two dimensional array of pixels, and the computerized image processing assembly being under control of a software program to process the two dimensional array of pixels to detect and analyze pigment agglomerates that protrude above the surface of the sample.

* * * * *

UNITED STATES PATENT AND TRADEMARK OFFICE

CERTIFICATE OF CORRECTION

PATENT NO. : 7,639,862 B2
APPLICATION NO. : 11/298958
DATED : December 29, 2009
INVENTOR(S) : Canning, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this

Ninth Day of November, 2010

David J. Kappos
*Director of the United States Patent and Trademark Office*